(12) United States Patent
Piazza et al.

(10) Patent No.: US 6,207,666 B1
(45) Date of Patent: Mar. 27, 2001

(54) METHOD FOR TREATING A PATIENT HAVING PRECANCEROUS LESION WITH 4-PHENYLPHTHALAZINE DERIVATIVES

(75) Inventors: Gary Piazza, Highlands Ranch, CO (US); Rifat Pamukcu, Spring House, PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/065,662

(22) Filed: Apr. 23, 1998

Related U.S. Application Data

(63) Continuation of application No. 08/473,094, filed on Jun. 7, 1995, now abandoned.

(51) Int. Cl.[7] .......................... A61K 31/495; A61K 31/50
(52) U.S. Cl. .................................................. 514/248
(58) Field of Search ................................ 514/248

(56) References Cited

FOREIGN PATENT DOCUMENTS

WO9846574 * 10/1998 (WO) .................... 514/248

OTHER PUBLICATIONS

Blaya, C. et al., Effect of the protein kinase inhibitors, 1–(5–isoquinolinylsulfonyl)–2–methylpiperazine H–7 and N–(2–[methlamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Consitutive Transcriptional Activation by a β–Catenin–Tcf Complex in APC Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

* cited by examiner

Primary Examiner—Jerome D. Goldberg
(74) Attorney, Agent, or Firm—Robert W. Stevenson

(57) ABSTRACT

Derivatives of 4-phenylphthalazine are useful for the treatment of patients having precancerous lesions. These compounds are also useful to inhibit the growth of neoplastic cells.

23 Claims, No Drawings

METHOD FOR TREATING A PATIENT HAVING PRECANCEROUS LESION WITH 4-PHENYLPHTHALAZINE DERIVATIVES

This application is a continuation of 08/473,094 filed Jun. 7, 1995 now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptotis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis and eliminating and inhibiting precancerous lesions, and neoplastic cells.

It was unexpectedly discovered that the compounds of this invention have growth inhibitory effects on neoplastic cells. Specifically, these compounds were unexpectedly found to induce apoptosis in neoplastic cells. Therefore, they are useful against precancerous conditions.

DETAILED DESCRIPTION OF THE INVENTION

As discussed above, this invention is a method of treating a patient with precancerous lesions or neoplasms by administering a pharmacologically effective amount of a compound of formula I below:

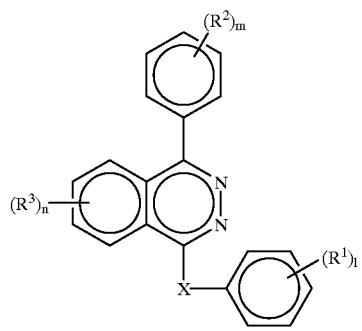

(I)

In the compounds of the present invention, $R^1$ is selected from an alkyl group, an alkoxy group, a halogen and a trihalomethyl group. More preferably $R^1$ may be selected from an alkoxy group and a halogen. Even more preferably, $R^1$ may be a halogen, and most preferably, $R^1$ may be chlorine. On the other hand, $R^2$ may preferably be selected from an alkyl group, an alkoxy group and a halogen, while $R^3$ may be an alkyl group.

"Alkyl group" refers to straight or branched chain $C_1$–$C_{12}$ groups such as methyl, ethyl, propyl, isopropyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine.

In the above formula [I], each of the integers represented by 1, m and n may be variable from zero to 3. But there are some restrictions depending on the species of X. When X represents NH group, the case where all of the integers are zero is excluded; in other words, there is at least one substituent on the aromatic nuclei. Thus, when X is NH, there are a number of possible combinations in number of the substituents on the aromatic nuclei. Among them, the following four combinations are found to be particularly preferred:

(1) l=1 to 3, m=n=zero;
(2) l=1 to 2, m=1 to 2, n=zero;
(3) l=1 to 2, m=zero, n=1 to 2; and
(4) l=m=zero, n=1 to 2.

When X represents O (an oxygen atom), both m and n are required to be zero, while 1 may be variable from 1 to 3. Also, when X is O, 1 is preferred to be 1 or 2, while m=n=0.

The compound represented by the formula [I] can also form a pharmaceutically acceptable salt through the reaction of the basic nitrogen thereof with an acid. For example, there may be mentioned salts with mineral acids such as hydrogen chloride, sulfuric acid, hydrobrobromic acid, phosphoric acid, etc. or methanesulfonic acid, toluenesulfonic acid, benzenesulfonic acid, acetic acid, glycolic acid, glucuronic acid, maleic acid, oxalic acid, ascorbic acid, citric acid, salicylic acid, and so on.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water.

Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

In the following, there are enumerated concrete examples of the compounds represented by the formula [I].

| COMPOUND NO. | NAME OF COMPOUND |
|---|---|
| (1) | 1-(4-Methylanilino)-4-phenylphthalazine |
| (2) | 1-(3-Methylanilino)-4-phenylphthalazine |
| (3) | 1-(2-Methylanilino)-4-phenylphthalazine |
| (4) | 1-(4-Ethylanilino)-4-phenylphthalazine |
| (5) | 1-(2-Ethylanilino)-4-phenylphthalazine |
| (6) | 1-(4-n-Butylanilino)-4-phenylphthalazine |
| (7) | 1-(3-n-Butylanilino)-4-phenylphthalazine |
| (8) | 1-(4-t-Butylanilino)-4-phenylphthalazine |
| (9) | 1-(4-Methoxyanilino)-4-phenylphthalazine |
| (10) | 1-(3-Methoxyanilino)-4-phenylphthalazine |
| (11) | 1-(3-Propoxyanilino)-4-phenylphthalazine |
| (12) | 1-(4-n-Butoxyanilino)-4-phenylphthalazine |
| (13) | 1-(4-Fluoroanilino)-4-phenylphthalazine |
| (14) | 1-(3-Fluoroanilino)-4-phenylphthalazine |
| (15) | 1-(2-Fluoroanilino)-4-phenylphthalazine |
| (16) | 1-(4-Chloroanilino)-4-phenylphthalazine |
| (17) | 1-(3-Chloroanilino)-4-phenylphthalazine |
| (18) | 1-(2-Chloroanilino)-4-phenylphthalazine |
| (19) | 1-(4-Bromoanilino)-4-phenylphthalazine |
| (20) | 1-(3-Bromoanilino)-4-phenylphthalazine |
| (21) | 1-(4-Iodoanilino)-4-phenylphthalazine |
| (22) | 1-(3-Iodoanilino)-4-phenylphthalazine |
| (23) | 1-(4-Ethoxycarbonylanilino)-4-phenylphthalazine |
| (24) | 1-(4-Carboxylanilino)-4-phenylphthalazine |
| (25) | 1-(4-Cyanoanilino)-4-phenylphthalazine |
| (26) | 1-(4-Acetylanilino)-4-phenylphthalazine |
| (27) | 1-(4-Trifluoromethylanilino)-4-phenylphthalazine |
| (28) | 1-(3-Trifluoromethylanilino)-4-phenylphthalazine |
| (29) | 1-(2-Trifluoromethylanilino)-4-phenylphthalazine |
| (30) | 1-(3-Hydroxylanilino)-4-phenylphthalazine |
| (31) | 1-(2,3-Dimethylanilino)-4-phenylphthalazine |
| (32) | 1-(2,4-Dimethylanilino)-4-phenylphthalazine |
| (33) | 1-(2,5-Dimethylanilino)-4-phenylphthalazine |
| (34) | 1-(3,4-Dimethylanilino)-4-phenylphthalazine |
| (35) | 1-(2,5-Diethylanilino)-4-phenylphthalazine |
| (36) | 1-(2,5-Dipropylanilino)-4-phenylphthalazine |
| (37) | 1-(2,5-Dimethoxyanilino)-4-phenylphthalazine |
| (38) | 1-(3,4-Dimethoxyanilino)-4-phenylphthalazine |
| (39) | 1-(2,5-Dichloroanilino)-4-phenylphthalazine |
| (40) | 1-(3,4-Dichloroanilino)-4-phenylphthalazine |
| (41) | 1-(2,5-Difluoroanilino)-4-phenylphthalazine |
| (42) | 1-(3-Chloro-4-methylanilino)-4-phenylphthalazine |
| (43) | 1-(2-Methyl-3-chloroanilino)-4-phenylphthalazine |
| (44) | 1-(2-Methyl-4-chloroanilino)-4-phenylphthalazine |
| (45) | 1-(3-Methyl-4-chloranilino)-4-phenylphthalazine |
| (46) | 1-(3-Fluoro-4-methylanilino)-4-phenylphthalazine |
| (47) | 1-(2-Methoxy-5-methylanilino)-4-phenylphthalazine |
| (48) | 1-(5-Chloro-2-methoxyanilino)-4-phenylphthalazine |
| (49) | 1-(2-Methyl-5-trifluoromethylanilino)-4-phenylphthalazine |
| (50) | 1-(2-Methoxy-5-trifluoromethylanilino)-4-phenylphthalazine |
| (51) | 1-(2,4,6-Trimethylanilino)-4-phenylphthalazine |
| (52) | 1-(3,4,5-Trimethoxyanilino)-4-phenylphthalazine |
| (53) | 1-Anilino-4-(4-methylphenyl)phthalazine |
| (54) | 1-(4-Methylanilino)-4-(4-methylphenyl)phthalazine |
| (55) | 1-(4-Butylanilino)-4-(4-methylphenyl)phthalazine |
| (56) | 1-(2,5-Dimethylanilino)-4-(4-methylphenyl)phthalazine |
| (57) | 1-(3-Methoxyanilino)-4-(4-methylphenyl)phthalazine |
| (58) | 1-(4-Butoxyanilino)-4-(4-methylphenyl)phthalazine |
| (59) | 1-(2,5-Dimethoxyanilino)-4-(4-methylphenyl)phthalazine |
| (60) | 1-(3-Chloroanilino)-4-(4-methylphenyl)phthalazine |
| (61) | 1-(3-Bromoanilino)-4-(4-methylphenyl)phthalazine |

| COMPOUND NO. | NAME OF COMPOUND |
|---|---|
| (62) | 1-(3-Fluoroanilino)-4-(4-methylphenyl)phthalazine |
| (63) | 4-(4-Methylphenyl)-1-(3-trifluoromethylaniliono)phthalazine |
| (64) | 1-(5-Chloro-2-methoxyanilino)-4-(4-methylphenyl)phthalazine |
| (65) | 1-(3-Chloro-4-methylanilino)-4-(4-methylphenyl)phthalazine |
| (66) | 1-(4-Ethoxycarbonylanilino)-4-(4-methylphenyl)phthalazine |
| (67) | 1-Anilino-4-(4-butylphenyl)phthalazine |
| (68) | 4-(4-Butylphenyl)-1-(2,5-dimethylanilino)phthalazine |
| (69) | 4-(4-Butylphenyl)-1-(2,5-dimethoxyanilino)phthalazine |
| (70) | 4-(4-Butylphenyl)-1-(3-chloroanilino)phthalazine |
| (71) | 4-(4-Butylphenyl)-1-(3-trifluoromethylanilino)phthalazine |
| (72) | 4-(4-Butylphenyl)-1-(5-chloro-2-methoxyanilino)phthalazine |
| (73) | 1-Anilino-4-(2,4-dimethylphenyl)phthalazine |
| (74) | 1-Anilino-4-(4-methoxyphenyl)phthalazine |
| (75) | 1-(4-Butylanilino)-4-(4-methoxyphenyl)phthalazine |
| (76) | 1-(2,5-Dimethylanilino)-4-(4-methoxyphenyl)phthalazine |
| (77) | 1-(2,5-Dimethoxyanilino)-4-(4-methoxyphenyl)phthalazine |
| (78) | 1-(3-Chloroanilino)-4-(4-methoxyphenyl)phthalazine |
| (79) | 4-(4-Methoxyphenyl)-1-(3-trifluoromethylanilino)phthalazine |
| (80) | 1-(5-Chloro-2-methoxyanilino)-4-(4-methoxyphenyl)phthalazine |
| (81) | 1-(4-ethoxycarbonylanilino)-4-(4-methoxyphenyl)phthalazine |
| (82) | 1-Anilino-4-(4-butoxyphenyl)phthalazine |
| (83) | 4-(4-Butoxyphenyl)-1-(2,5-dimethylanilino)phthalazine |
| (84) | 4-(4-Butoxyphenyl)-1-(2,5-dimethoxyanilino)phthalazine |
| (85) | 4-(4-Butoxyphenyl)-1-(3-chloroanilino)phthalazine |
| (86) | 4-(4-Butoxyphenyl)-1-(3-trifloromethylanilino)phthalazine |
| (87) | 4-(4-Butoxyphenyl)-1-(5-chloro-2-methoxyanilino)phthalazine |
| (88) | 1-Anilino-4-(2,4-dimethoxyphenyl)phthalazine |
| (89) | 1-2,5-Dimethylanilino)-4-(2,4-dimethoxyphenyl)phthalazine |
| (90) | 1-(2,5-Dimethoxyanilino)-4-(2,4-dimethoxyphenyl)phthalazine |
| (91) | 1-(3-Chloroanilino)-4-(2,4-dimethoxyphenyl)phthalazine |
| (92) | 4-(2,4-Dimethoxyphenyl)-1-(3-trifluoromethylanilino)-phthalazine |
| (93) | 1-(5-Chloro-2-methoxyanilino)-4-(2,4-dimethoxyphenyl)-phthalazine |
| (94) | 1-Anilino-4-(4-chlorophenyl)phthalazine |
| (95) | 4-(4-Chlorophenyl)-1-(2,5-dimethylanilino)phthalazine |
| (96) | 4-(4-Chlorophenyl)-1-(2,5-dimethoxyanilino)phthalazine |
| (97) | 1-(3-Chloroanilino)-4-(4-chlorophenyl)-phthalazine |
| (98) | 4-(4-Chlorophenyl)-1-(3-trifluoromethylanilino)phthalazine |
| (99) | 1-(5-Chloro-2-methoxyanilino)-4-(4-chlorophenyl)phthalazine |
| (100) | 1-Anilino-4-(4-bromophenyl)phthalazine |
| (101) | 1-Anilino-4-(4-fluorophenyl)phthalazine |
| (102) | 1-(2,5-Dimethylanilino)-4-(4-fluorophenyl)phthalazine |
| (103) | 1-(2,5-Dimethoxyanilino)-4-(4-fluorophenyl)phthalazine |
| (104) | 1-(3-Chloroanilino)-4-(4-fluorophenyl)phthalazine |
| (105) | 4-(4-Fluorophenyl)-1-(3-trifluoromethylanilino)phthalazine |
| (106) | 1-(5-Chloro-2-methoxyanilino)-4-(4-fluorophenyl)phthalazine |
| (107) | 1-Anilino-4-(4-ethoxycarbonylphenyl)phthalazine |
| (108) | 1-(2,5-Dimethylanilino)-4-(4-ethoxycarbonylphenyl)phthalazine |
| (109) | 1-(2,5-Dimethoxyanilino)-4-(4-ethoxycarbonylphenyl)phthalazine |
| (110) | 1-(3-Chloroanilino)-4-(4-ethoxycarbonylphenyl)phthalazine |
| (111) | 4-(4-Ethoxycarbonylphenyl)-1-(3-trifluoromethylanilino)phthalazine |
| (112) | 1-(5-Chloro-2-methoxyanilino)-4-(4-ethoxycarbonylphenyl)phthalazine |
| (113) | 1-Anilino-6-methyl-4-phenylphthalazine |
| (114) | 1-Anilino-7-methyl-4-phenylphthalazine |
| (115) | 1-(2,5-Dimethylanilino)-6-methyl-4-phenylphthalazine |
| (116) | 1-(2,5-Dimethylanilino)-7-methyl-4-phenylphthalazine |
| (117) | 1-(2,5-Dimethoxyanilino)-6-methyl-4-phenylphthalazine |
| (118) | 1-(2,5-Dimethoxyanilino)-7-methyl-4-phenylphthalazine |
| (119) | 1-(3-Chloroanilino)-6-methyl-4-phenylphthalazine |
| (120) | 1-(3-Chloroanilino)-7-methyl-4-phenylphthalazine |
| (121) | 6-Methyl-4-phenyl-1-(3-trifuoromethylanilino)phthalazine |
| (122) | 7-Methyl-4-phenyl-1-(3-trifluoromethylanilino)phthalazine |
| (123) | 1-(5-Chloro-2-methoxyanilino)-6-methyl-4-phenylphthalazine |
| (124) | 1-(5-Chloro-2-methoxyanilino)-7-methyl-4-phenylphthalazine |
| (125) | 1-Anilino-6,7-dimethyl-4-phenylphthalazine |
| (126) | 1-(4-Butylanilno)-6,7-dimethyl-4-phenylphthalazine |
| (127) | 1-(2,5-Dimethylanilino)-6,7-dimethyl-4-phenylphthalazine |
| (128) | 1-(2,5-Dimethoxyanilino)-6,7-dimethyl-4-phenylphthalazine |
| (129) | 1-(4-Butoxyanilino)-6,7-dimethyl-4-phenylphthalazine |
| (130) | 1-(3-Chloroanilino)-6,7-dimethyl-4-phenylphthalazine |
| (131) | 6,7-Dimethyl-4-phenyl-1-(3-trifluoromethylanilino)phthalazine |
| (132) | 1-(5-Chloro-2-methoxyanilino)-6,7-dimethyl-4-phenylphthalazine |
| (133) | 1-(3-Chloro-4-methylanilino)-6,7-dimethyl-4-phenylphthalazine |
| (134) | 6,7-Dimethyl-1-(4-ethoxycarbonylanilino)-4-phenylphthalazine |
| (135) | 1-Anilino-5,8-dimethyl-4-phenylphthalazine |
| (136) | 1-(3-Chloroanilino)-5,8-dimethyl-4-phenylphthalazine |
| (137) | 1-Anilino-6,7-dibutyl-4-phenylphthalazine |
| (138) | 1-Anilino-6,7-dimethoxy-4-phenylphthalazine |
| (139) | 6,7-Dimethoxy-1-(2,5-dimethylanilino)-4-phenylphthalazine |
| (140) | 6,7-Dimethoxy-1-(2,5-dimethoxyanilino)-4-phenylphthalazine |
| (141) | 1-(3-Chloroanilino)-6,7-dimethoxy-4-phenylphthalazine |
| (142) | 6,7-Dimethoxy-4-phenyl-1-(3-trifluoromethylanilino)phthalazine |
| (143) | 1-(5-Chloro-2-methoxyanilino)-6,7-dimethoxy-4-phenylphthalazine |
| (144) | 1-(4-Butylanilino)-6,7-dimethoxy-4-phenylphthalazine |

-continued

| COMPOUND NO. | NAME OF COMPOUND |
|---|---|
| (145) | 1-(4-Butoxyanilino)-6,7-dimethoxy-4-phenylphthalazine |
| (146) | 1-Anilino-5,8-dimethoxy-4-phenylphthalazine |
| (147) | 1-Anilino-6,7-dibutoxy-4-phenylphthalazine |
| (148) | 1-Anilino-6,7-dichloro-4-phenylphthalazine |
| (149) | 6,7-Dichloro-1-(2,5-dimethylanilino)-4-phenylphthalazine |
| (150) | 6,7-Dichloro-1-(2,5-dimethoxyanilino)-4-phenylphthalazine |
| (151) | 1-(3-Chloroanilino)-6,7-dichloro-4-phenylphthalazine |
| (152) | 6,7-Dichloro-4-phenyl-1-(3-trifluoromethylanilino)phthalazine |
| (153) | 1-(4-Chloro-2-methoxyanilino)-6,7-dichloro-4-phenylphthalazine |
| (154) | 1-Anilino-5,8-dichloro-4-phenylphthalazine |
| (155) | 1-Anilino-6-ethoxycarbonyl-4-phenylphthalazine |
| (156) | 1-Anilino-6,7-dimethyl-4-(4-methylphenyl)phthalazine |
| (157) | 1-(4-Butylanilino)-6,7-dimethyl-4-(4-methylphenyl)phthalazine |
| (158) | 6,7-Dimethyl-1-(2,5-dimethylanilino)-4-(4-methylphenyl)phthalazine |
| (159) | 6,7-Dimethyl-1-(3-methoxyanilino)-4-(4-methylphenyl)phthalazine |
| (160) | 1-(2,5-Dimethoxyanilino)-6,7-dimethyl-4-(4-methylphenyl)-phthalazine |
| (161) | 1-(3-Chloroanilino)-6,7-dimethyl-4-(4-methylphenyl)phthalazine |
| (162) | 6,7-Dimethyl-4-(methylphenyl)-1-(3-trifluoromethylanilino)phthalazine |
| (163) | 1-(4-Chloro-2-methoxyanilino)-6,7-dimethyl-4-(4-methylphenyl)phthalazine |
| (164) | 6,7-Dimethyl-1-(4-ethoxycarbonylanilino)-4-(4-methylphenyl)phthalazine |
| (165) | 1-Anilino-4-(4-butylphenyl)-6,7-dimethylphthalazine |
| (166) | 1-Anilino-6,7-dimethyl-4-(4-methoxyphenyl)phthalazine |
| (167) | 6,7-Dimethyl-1-(2,5-dimethylanilino)-4-(4-methoxyphenyl)phthalazine |
| (168) | 1-(2,5-Dimethoxyanilino)-6,7-dimethyl-4-(4-methoxyphenyl)phthalazine |
| (169) | 1-(3-Chloroanilino)-6,7-dimethyl-4-(4-methoxyphenyl)phthalazine |
| (170) | 6,7-Dimethyl-4-(4-methoxyphenyl)-1-(3-trifluoromethylanilino)phthalazine |
| (171) | 1-(5-Chloro-2-methoxyanilino)-6,7-dimethyl-4-(4-methoxyphenyl)phthalazine |
| (172) | 1-Anilino-4-(4-butoxyphenyl)-6,7-dimethylphthalazine |
| (173) | 1-Anilino-4-(2,4-dimethoxyphenyl)-6,7-dimethylphthalazine |
| (174) | 1-Anilino-4-(4-chlorophenyl)-6,7-dimethylphthalazine |
| (175) | 1-(3-Chloroanilino)-4-(4-chlorophenyl)-6,7-dimethylphthalazine |
| (176) | 1-(3-Chloro-4-methyanilino)-4-(4-chlorophenyl)-6,7-dimethylphthalazine |
| (177) | 1-Anilino-6,7-dimethyl-4-(4-fluorophenyl)phthalazine |
| (178) | 1-Anilino-6,7-dimethyl-4-(4-ethoxycarbonylphenyl)phthalazine |
| (179) | 1-Anilino-6,7-dimethoxy-4-(4-methylphenyl)phthalazine |
| (180) | 6,7-Dimethoxy-1-(2,5-dimethylanilino)-4-(4-methylphenyl)phthalazine |
| (181) | 6,7-Dimethoxy-1-(2,5-dimethoxyanilino)-4-(4-methylphenyl)phthalazine |
| (182) | 1-(3-Chloroanilino)-6,7-dimethoxy-4-(4-methylphenyl)phthalazine |
| (183) | 1-Anilino-4-(4-butylphenyl)-6,7-dimethoxyphthalazine |
| (184) | 1-Anilino-6,7-dimethoxy-4-(4-methoxyphenyl)phthalazine |
| (185) | 1-Anilino-6,7-dimethoxy-4-(2,4-dimethoxyphenyl)phthalazine |
| (186) | 1-Anilino-4-(4-chlorophenyl)-6,7-dimethoxyphthalazine |
| (187) | 1-Anilino-6,7-dimethoxy-4-(4-fluorophenyl)phthalazine |
| (188) | 1-Anilino-6,7-dimethoxy-4-(4-ethoxycarbonylphenyl)phthalazine |
| (189) | 1-Anilino-6,7-dichloro-4-(4-methylphenyl)phthalazine |
| (190) | 1-Anilino-4-(4-butylphenyl)-6,7-dichlorophthalazine |
| (191) | 1-Anilino-6,7-dichloro-4-(4-methoxyphenyl)phthalazine |
| (192) | 1-Anilino-4-(4-butoxyphenyl)-6,7-dichlorophthalazine |
| (193) | 1-Anilino-6,7-dichloro-4-(2,4-dimethoxyphenyl)phthalazine |
| (194) | 1-Anilino-4-(4-chlorophenyl)-6,7-dichlorophthalazine |
| (195) | 1-Anilino-6,7-dichloro-4-(4-fluorophenyl)phthalazine |
| (196) | 1-Anilino-6,7-dichloro-4-(4-ethoxycarbonylphenyl)phthalazine |
| (197) | 1-Anilino-4-(4-carboxyphenyl)phthalazine |
| (198) | 4-(4-Carboxyphenyl)-1-(2,5-dimethylanilino)phthalazine |
| (199) | 4-(4-Carboxyphenyl)-1-(2,5-dimethoxyanilino)phthalazine |
| (200) | 4-(4-Carboxyphenyl)-1-(3-chloroanilino)phthalazine |
| (201) | 4-(4-Carboxyphenyl)-1-(3-trifluoromethylanilino)phthalazine |
| (202) | 4-(4-Carboxyphenyl)-1-(5-chloro-2-methoxyanilino)phthalazine |
| (203) | 1-Anilino-4-(4-hydroxyphenyl)phthalazine |
| (204) | 1-(2,5-Dimethylanilino)-4-(4-hydroxyphenyl)phthalazine |
| (205) | 1-(2,5-Dimethylanilino)-4-(4-hydroxyphenyl)phthalazine |
| (206) | 1-(3-Chloroanilino)-4-(4-hydroxyphenyl)phenylphthalazine |
| (207) | 4-(4-Hydroxyphenyl)-1-(3-trifluoromethylanilino)phenylphthalazine |
| (208) | 1-(5-Chloro-2-methoxyanilino)-4-(4-carboxyphenyl)phenylphthalazine |
| (209) | 1-(4-Acetylanilino)-4-(4-methylphenyl)phenylphthalazine |
| (210) | 1-(4-Acetylanilino)-6,7-dimethyl-4-phenylphthalazine |
| (211) | 1-(4-Methylphenoxy)-4-phenylphthalazine |
| (212) | 1-(3-Methylphenoxy)-4-phenylphthalazine |
| (213) | 1-(2-Methylphenoxy)-4-phenylphthalazine |
| (214) | 1-(4-Ethylphenoxy)-4-phenylphthalazine |
| (215) | 1-(2-Ethylphenoxy)-4-phenylphthalazine |
| (216) | 1-(4-n-Butylphenoxy)-4-phenylphthalazine |
| (217) | 1-(3-Butylphenoxy)-4-phenylphthalazine |
| (218) | 1-(4-t-Butylphenoxy)-4-phenylphthalazine |
| (219) | 1-(4-Methoxyphenoxy)-4-phenylphthalazine |
| (220) | 1-(3-Methoxyphenoxy)-4-phenylphthalazine |
| (221) | 1-(3-Propoxyphenoxy)-4-phenylphthalazine |
| (222) | 1-(3-Butoxyphenoxy)-4-phenylphthalazine |
| (223) | 1-(4-Fluorophenoxy)-4-phenylphthalazine |
| (224) | 1-(3-Fluorophenoxy)-4-phenylphthalazine |
| (225) | 1-(4-Chlorophenoxy)-4-phenylphthalazine |
| (226) | 1-(3-Chlorophenoxy)-4-phenylphthalazine |
| (227) | 1-(2-Chlorophenoxy)-4-phenylphthalazine |
| (228) | 1-(4-Bromophenoxy)-4-phenylphthalazine |
| (229) | 1-(3-Bromophenoxy)-4-phenylphthalazine |
| (230) | 1-(4-Ethoxycarbonylphenoxy)-4-phenylphthalazine |
| (231) | 1-(4-Ethoxycarbonylphenoxy)-4-phenylphthalazine |
| (232) | 1-(4-Carboxyphenoxy)-4-phenylphthalazine |
| (233) | 1-(4-Cyanophenoxy)-4-phenylphthalazine |
| (234) | 1-(4-Acetylphenoxy)-4-phenylphthalazine |

-continued

| COMPOUND NO. | NAME OF COMPOUND |
|---|---|
| (235) | 1-(4-Trifluoromethylphenoxy)-4-phenylphthalazine |
| (236) | 1-(3-Trifluoromethylphenoxy)-4-phenylphthalazine |
| (237) | 1-(3-Hydroxyphenoxy)-4-phenylphthalazine |
| (238) | 1-(2,3-Dimethylphenoxy)-4-phenylphthalazine |
| (239) | 1-(2,5-Dimethylphenoxy)-4-phenylphthalazine |
| (240) | 1-(2,5-Diethylphenoxy)-4-phenylphthalazine |
| (241) | 1-(2,5-Dipropylphenoxy)-4-phenylphthalazine |
| (242) | 1-(2,5-Dimethoxyphenoxy)-4-phenylphthalazine |
| (243) | 1-(3,4-Dimethoxyphenoxy)-4-phenylphthalazine |
| (244) | 1-(2,5-Dichlorophenoxy)-4-phenylphthalazine |
| (245) | 1-(2,6-Dichlorophenoxy)-4-phenylphthalazine |
| (246) | 1-(2,5-Difluorophenoxy)-4-phenylphthalazine |
| (247) | 1-(3-Chloro-4-methylphenoxy)-4-phenylphthalazine |
| (248) | 1-(3-Methyl-4-chlorophenoxy)-4-phenylphthalazine |
| (249) | 1-(3-Fluoro-4-methylphenoxy)-4-phenylphthalazine |
| (250) | 1-(2-Methoxy-4-chlorophenoxy)-4-phenylphthalazine |
| (251) | 1-(2-Methoxy-5-methylphenoxy)-.4-phenylphthalazine |
| (252) | 1-(2-Methyl-4-trifluoromethylphenoxy)-4-phenylphthalazine |
| (253) | 1-(2,4,6-Trimethylphenoxy)-4-phenylphthalazine |

Process for preparation of the compound [I]

The compound represented by the formula [I] can be prepared according to any suitable process, which is not particularly limited. Preferably, however, the compound [I] can be synthesized by the following reaction route:

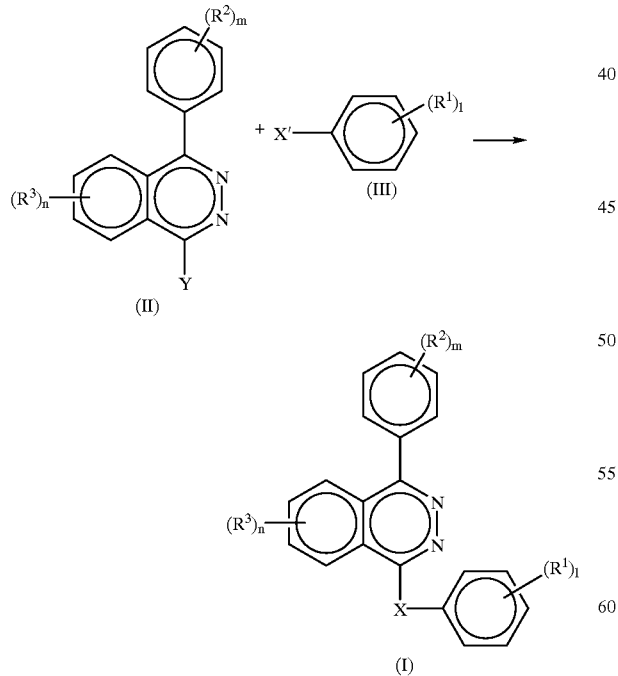

In the above formula, X' represents —$NH_2$ or OH; Y a halogen atom (e.g., chlorine, bromine or iodine), a group of the formula: —$S(O)_p$—$R^4$ (P=0 to 2, $R^4$ is a $C_{1-5}$ alkyl, phenyl or a substituted phenyl) or a group of the formula: —$OR^5$ ($R^5$ is a $C_{1-5}$ alkyl, phenyl or a substituted phenyl); and all of the other symbols have the same meanings as defined above.

According to this process, the starting compound represented by the formula (II), namely 1-chloro-4-phenylphthalazine or its derivative, is allowed to react with a benzene derivative represented by the formula (III), in either the presence or absence of a solvent, preferably in the presence of a catalyst, to prepare a 4-phenylphthalazine derivative represented by the formula [I].

The starting materials, i.e., 1-chloro-4-phenylphthalazine (II) or derivatives thereof were synthesized according to the method as described in Journal of Pharmacology, Vol. 86, p. 576 (1966), or the methods similar thereto.

As the benzene derivative (III) to be reacted with the compound (II) as mentioned above, there may be employed suitable substituted anilines or substituted phenols.

The reaction temperature may be in the range from −20 to 250° C., preferably from −10 to 180° C. The reaction time may be from 5 minutes to 24 hours, preferably from 10 minutes to 10 hours.

When a catalyst is to be employed, there may be used an organic base such as ammonia, triethylamine, piperidine or pyridine, or an inorganic base such as sodium carbonate, potassium carbonate, sodium hydroxide, potassium hydroxide, sodium hydride or sodium amide may be added at a molar ratio relative to the compound (II) in the range from 0.5 to 5, preferably from 1 to 3. Alternatively, it is also possible to use a metal such as copper, magnesium, cadmium, sodium or potassium, at a molar ratio relative to the compound (II) in the range from 0.001 to 2, preferably from 0.01 to 1.5.

When a solvent is to be employed, there may be used a solvent selected from ethers such as ethyl ether, tetrahydrofuran, and dioxane; halogenated alkanes such as chloroform, methylene chloride, etc.; alcohols such as methanol, ethanol, etc.; aromatic hydrocarbons such as benzene, toluene, xylene, etc.; amides such as demethylformamide, dimethylacetamide, etc.; and dimethylsulfoxide; and so on.

The compound (III) may be used in an amount of 0.5 to 30 moles, preferably 1 to 20 moles, per mole of the compound (II).

After completion of the reaction, the reaction mixture may be poured into a large excess of water or dissolved as such in a solvent such as chloroform to be neutralized therein. If desired, the precipitated crystals may be collected by filtration after concentration, or alternatively the product may be extracted with a suitable solvent such as chloroform when there is no precipitation, followed by recrystallization or chromatography according to conventional procedures.

The present invention is further illustrated by the following Examples, by which the present invention is not limited.

EXAMPLE 1

Synthesis of 1-(4-methylanilino)-4-phenylphthalazine (Compound No. 1)

To 2.41 g of 1-chloro-4-phenylphthalazine, there were added 5.35 g of p-toluidine and 70 mg of copper powders. The mixture was then subjected to stirring under heating for one hour while maintaining the reaction temperature at 100° C. After the reaction mixture was left to cool, a large excess of chloroform was added thereto. The resultant insolubles were filtered off and the filtrate was washed with a 5% aqueous sodium hydroxide and then with water. The organic layer was dried and concentrated, and the residue was recrystallized from ethanol to give 910 mg (yield: 29%) of pale yellow crystals.

M.P.: 185–186° C.

I.R.: 1630 cm$^{-1}$, 1510 cm$^{-1}$, 1410 cm$^{-1}$

M.S.: 310 (M±1)

EXAMPLE 2–30

The compounds as shown in Table 1 were synthesized according to the methods similar to Example 1.

TABLE 1

| Example | Compound No. | m.p./° C. | I.R./cm$^{-1}$ | M.S. |
|---|---|---|---|---|
| 2 | (2) | 202~203 | 3270, 1575, 1520, 1410, 790 | 310 (M ± 1) |
| 3 | (3) | 188 | 3200, 1500, 1400, 1200, 755 | 311 (M$^+$) 296 |
| 4 | (4) | 206~207 | 2990, 1625, 1520, 1420, 780 | 324 (M ± 1) |
| 5 | (6) | 189~190 | 2860, 1620, 1520, 1420, 780 | 353 (M$^+$) 310 |
| 6 | (9) | 206~207.5 | 2950, 1640, 1510, 1420, 1240, 785 | 327 (M$^+$) 312 |
| 7 | (10) | 196 | 3000, 1610, 1500, 1400, 1155, 780 | 326 (M ± 1) |
| 8 | (12) | 168.5~169 | 2950, 1620, 1505, 1410, 1240, 790 | 369 (M$^+$) 312 |
| 9 | (13) | 206~207 | 3050, 1620, 1520, 1410, 1220, 780 | 314 (M ± 1) |
| 10 | (14) | 239~240 | 3280, 1620, 1520, 1400, 1140, 790 | 314 (M ± 1) |
| 11 | (16) | 193~194 | 1620, 1580, 1500, 1400, 820, 770 | 330 (M$^+$) 332 |
| 12 | (17) | 191~194 | 1600, 1510, 1420, 1390, 770 | 330 (M$^+$) 332 |
| 13 | (18) | 170~171.5 | 3440, 1600, 1520, 1400, 1040, 760 | 330 (M$^+$) 332 |
| 14 | (19) | 219~222 | 3000, 1625, 1510, 1400, 820, 760 | 376 (M ± 1) |
| 15 | (23) | 236~237.5 | 3000, 1720, 1615, 1520, 1410, 1280 | 369 (M$^+$) 368 |
| 16 | (25) | 240~242.5 | 3360, 2210, 1610, 1510, 1410, 790 | 321 (M ± 1) |
| 17 | (26) | 247~248.5 | 3400, 1680, 1600, 1520, 1400, 1280 | 338 (M ± 1) |
| 18 | (28) | 174~175.5 | 3040, 1630, 1520, 1410, 1340, 1100 | 364 (M ± 1) |
| 19 | (31) | 240~242 | 3200, 1520, 1415, 790, 770 | 325 (M$^+$) 310 |
| 20 | (32) | 206.5~207.5 | 3400, 1500, 1400, 810, 780 | 325 (M$^+$) 310 |

TABLE 1-continued

| Example | Compound No. | m.p./° C. | I.R./cm$^{-1}$ | M.S. |
|---|---|---|---|---|
| 21 | (33) | 202~203.5 | 3200, 1500, 1400, 810, 780 | 325 (M$^+$) 310 |
| 22 | (34) | 204~204.5 | 3200, 1510, 1420, 790, 770 | 324 (M ± 1) |
| 23 | (37) | 215~216 | 3400, 1610, 1520, 1430, 790 | 357 (M$^+$) 326 |
| 24 | (43) | 217 | 1590, 1510, 1410, 780, 700 | 347 (M$^+$) 345 |
| 25 | (44) | 232~232.5 | 3400, 1490, 1400, 820, 780, 700 | 347 (M$^+$) 345 |
| 26 | (42) | 171~172 | 3000, 1610, 1500, 1400, 775, 700 | 346 (M ± 1) 344 |
| 27 | (47) | 129~132 | 3450, 1530, 1430, 1230, 790, 710 | 341 (M$^+$) 310 |
| 28 | (48) | 74.5~75 | 1600, 1500, 1420, 1220, 790, 780 | 364 (M$^+$) 362 |
| 29 | (51) | 200~202.5 | 3200, 1500, 1400, 780, 700 | 339 (M$^+$) |
| 30 | (24) | 250< | 3360, 1680, 1600, 1520, 1410, 780 | 340 (M ± 1) |

EXAMPLE 1

Synthesis of 1-(2-methylphenoxy)-4-phenylphthalazine (Compound No. 213)

To 1.20 g of 1-chloro-4-phenylphthalazine, there were added 5.40 g of o-cresol and 360 mg of potassium hydroxide. The resultant mixture was subjected to stirring under heating for 2 hours, while maintaining the reaction temperature at 100° C. After the reaction mixture was poured into 12 ml of an aqueous solution having 3.6 g of potassium hydroxide dissolved therein the crystals precipitated were recovered by filtration. The crude crystals were dissolved in chloroform, washed with water, dried and concentrated. The residue was recrystallized from ethanol-n-hexane to give 725 mg (yield: 46%) of white crystals.

m.p.: 136.5–137.5° C.

I.R.: 1490 cm$^{-1}$, 1385 cm$^{-1}$, 1230 cm$^{-1}$, 1190 cm$^{-1}$, 790 cm$^{-1}$, 750 cm$^{-1}$.

M.S.: 312 (M$^+$)

EXAMPLES 32–44

According to procedures similar to that as described in Example 31, there were synthesized the compounds as shown in Table 2.

TABLE 2

| Example | Compound No. | m.p./° C. | I.R./cm$^{-1}$ | M.S. |
|---|---|---|---|---|
| 32 | (212) | 148~150 | 1490, 1390, 1250, 1165, 800, 770 | 312 (M$^+$) 295 |

TABLE 2-continued

| Example | Compound No. | m.p./° C. | I.R./cm$^{-1}$ | M.S. |
|---|---|---|---|---|
| 33 | (214) | 171.5~172 | 1510, 1385, 1210, 850, 770, 700 | 326 (M$^+$), 311 |
| 34 | (218) | 211~212.5 | 2970, 1500, 1390, 1230, 790 | 354 (M$^+$), 339 |
| 35 | (219) | 163~164 | 1510, 1390, 1205, 1030, 850, 700 | 328 (M$^+$), 121 |
| 36 | (227) | 171~172 | 1550, 1480, 1380, 1230, 790, 780 | 331 (M ± 1), 297 |
| 37 | (228) | 179~180 | 1490, 1380, 1220, 1010, 790 | 376 (M$^+$), 378 |
| 38 | (234) | 139~141.5 | 1700, 1600, 1380, 1220, 850, 800 | 340 (M$^+$), 325 |
| 39 | (236) | 119~121 | 1450, 1385, 1330, 1170, 1120, 900 | 366 (M$^+$), 365 |
| 40 | (226) | 149~149.5 | 1595, 1380, 1220, 890, 795, 700 | 332 (M$^+$), 334 |
| 41 | (239) | 153~155 | 1570, 1385, 1250, 1120, 770 | 326 (M$^+$), 309 |
| 42 | (248) | 155.5~156 | 1480, 1390, 1240, 1170, 1050, 790 | 346 (M$^+$), 348 |
| 43 | (244) | 175.5~176.5 | 1580, 1470, 1365, 1220, 1090, 770 | 365 (M ± 1), 331 |
| 44 | (245) | 210~210.5 | 1450, 1380, 1360, 1240, 770 | 366 (M$^+$), 331 |

EXAMPLE 45

Synthesis of 1- (3-chloroanilino) -4- (4-methylphenyl) phthalazime (Compound No. 60)

To 172 mg of 1-chloro-4-(4-methylphenyl) phthalazine, there was added 319 mg of m-chloroaniline, and the resultant mixture was heated at 100° C. with stirring for one hour. After the reaction mixture was left to cool to room temperature, a large excess of chloroform was added thereto, followed by washing with a 5% aqueous sodium hydroxide and then with water. The organic layer was dried and subjected to concentration. The residue was recrystallized from ethanol to give 145 mg (yield: 62%) of pale yellow crystals.

m.p.: 211.5–212° C.

I.R.: 595 cm$^{-1}$, 1510 cm$^{-1}$, 1475 cm$^{-1}$, 1405 cm$^{-1}$, 770 cm$^{-1}$

M.S.: 345 (M$^+$), 343 (M$^+$), 344

EXAMPLES 46–109

The compounds as shown in Table 3, having the following formula:

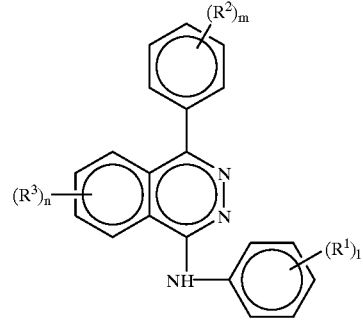

were prepared according to the procedures similarly as described in Example 45.

TABLE 3

| Example | Compound No. | R$^1$ | R$^2$ | R$^3$ | m.p./° C. | I.R./cm$^{-1}$ | MS |
|---|---|---|---|---|---|---|---|
| 46 | (63) | 3-CF$_3$ | 4-CH$_3$ | H | 179–180 | 3240, 1595, 1510, 1400, 1330, 1160 | 379 (M$^+$), 378 |
| 47 | (56) | 2-CH$_3$, 5-CH$_3$ | 4-CH$_3$ | H | 184–185 | 3200, 1610, 1490, 1405, 1020 | 339 (M$^+$), 324 |
| 48 | (59) | 2-OCH$_3$, 5-OCH$_3$ | 4-CH$_3$ | H | 192.5–193 | 3435, 1600, 1510, 1420, 1200, 1035 | 371 (M$^+$), 340 |
| 49 | (64) | 2-OCH$_3$, 4-Cl | 4-CH$_3$ | H | 197–197.5 | 3430, 1595, 1510, 1420, 1240, 1010 | 377 (M$^+$), 375 (M$^+$) |
| 50 | (78) | 3-Cl | 4-OCH$_3$ | H | 227–228 | 1600, 1480, 1400, 1250, 770 | 363 (M$^+$), 361 (M$^+$), 360 |
| 51 | (79) | 3-CF$_3$ | 4-OCH$_3$ | H | 228–229 | 3230, 1610, 1515, 1405, 1335, 1250 | 395 (M$^+$), 394 |
| 52 | (76) | 2-CH$_3$, 5-CH$_3$ | 4-OCH$_3$ | H | 179–180 | 1610, 1490, 1400, 1250, 1175 | 355 (M$^+$), 340 |

TABLE 3-continued

| Example | Compound No. | R¹ | R² | R³ | m.p./° C. | I.R./cm⁻¹ | MS |
|---|---|---|---|---|---|---|---|
| 53 | (77) | 2-OCH₃, 5-OCH₃ | 4-OCH₃ | H | 185–186 | 3435, 1610, 1515, 1250, 1020 | 387 (M⁺) 356 |
| 54 | (80) | 2-OCH₃, 4-Cl | 4-OCH₃ | H | 206–207 | 3435, 1600, 1515, 1420, 1250, 1020 | 393 (M⁺) 391 (M⁺) |
| 55 | (97) | 3-Cl | 4-Cl | H | 222–223 | 1600, 1480, 1410, 1080, 780 | 367 (M⁺) 365 (M⁺) 364 |
| 56 | (98) | 3-CF₃ | 4-Cl | H | 180–181 | 3270, 1605, 1450, 1415, 1340, 1120 | 401 (M⁺) 399 (M⁺) 398 |
| 57 | (95) | 2-CH₃, 5-CH₃ | 4-Cl | H | 196–197 | 1580, 1500, 1410, 1090, 835 | 361 (M⁺) 359 (M⁺) 344 |
| 58 | (96) | 2-OCH₃, 5-OCH₃ | 4-Cl | H | 190–192 | 3440, 1600, 1510, 1430, 1220, 1045 | 393 (M⁺) 391 (M⁺) 360 |
| 59 | (99) | 2-OCH₃, 4-Cl | 4-Cl | H | 200–201 | 3420, 1600, 1410, 900, 770 | 397 (M⁺) 395 (M⁺) 364 |
| 60 | (70) | 3-Cl | 4-C₄H₉ | H | 193–194 | 2920, 1600, 1410, 900, 770 | 389 (M⁺) 387 (M⁺) 386 |
| 61 | (71) | 3-CF₃, 5-CH₃ | 4-C₄H₉ | H | 164–167 | 2920, 1610, 1410, 1330, 1170, 1120 | 421 (M⁺) 420 |
| 62 | (68) | 2-CH₃, 5-CH₃ | 4-C₄H₉ | H | 169.5–171 | 2920, 1610, 1490, 1400, 805, 775 | 381 (M⁺) 366 |
| 63 | (69) | 2-OCH₃ | 4-C₄H₉ | H | 159.5–160 | 2920, 1610, 1520, 1430, 1205, 785 | 413 (M⁺) 382 |
| 64 | (72) | 2-OCH₃, 5-Cl | 4-C₄H₉ | H | 173.5–174.5 | 3440, 2920, 1595, 1510, 1420, 1250 | 419 (M⁺) 417 (M⁺) 396 |
| 65 | (85) | 3-Cl | 4-OC₄H₉ | H | 184.5–185.5 | 2950, 1600, 1515, 1420, 1250, 770 | 405 (M⁺) 403 (M⁺) 402 |
| 66 | (86) | 3-CF₃ | 4-OC₄H₉ | H | 183–184 | 2950, 1610, 1510, 1400, 1330, 1110 | 437 (M⁺) 438 |
| 67 | (83) | 2-CH₃, 5-CH₃ | 4-OC₄H₉ | H | 156.5–158 | 2950, 1610, 1500, 1400, 1250 | 397 (M⁺) 382 |
| 68 | (84) | 2-OCH₃, 5-OCH₃ | 4-OC₄H₉ | H | 163–163.5 | 3440, 2950, 1605, 1505, 1240 | 429 (M⁺) 398 |
| 69 | (87) | 2-OCH₃, 5-Cl | 4-OC₄H₉ | H | 181.5–182.5 | 3420, 2950, 1600, 1510, 1410, 1250 | 435 (M⁺) 433 (M⁺) 402 |
| 70 | (104) | 3-Cl | 4-F | H | 228.5–229.5 | 1600, 1515, 1420, 1220, 1150, 775 | 351 (M⁺) 349 (M⁺) 348 |
| 71 | (104) | 3-Cl | 4-F | H | 205–206.5 | 1610, 1520, 1420, 1335, 1120, 800 | 383 (M⁺) 382 |
| 72 | (102) | 2-CH₃, 5-CH₃ | 4-F | H | 188.5–189.5 | 1600, 1500, 1415, 1225 | 343 (M⁺) 328 |
| 73 | (103) | 2-OCH₃, 5-OCH₃ | 4-F | H | 176–177 | 3445, 1600, 1510, 1430, 1210, 1020 | 375 (M⁺) 344 |
| 74 | (106) | 2-OCH₃, 5-Cl | 4-F | H | 216–217 | 3445, 1600, 1515, 1430, 1240, 1015 | 381 (M⁺) 379 (M⁺) 348 |
| 75 | (91) | 3-Cl | 2-OCH₃, 4-OCH₃ | H | 200–201.5 | 1600, 1485, 1400, 1215, 1160, 775 | 393 (M⁺) 391 (M⁺) |
| 76 | (92) | 3-CF₃ | 2-OCH₃, 4-OCH₃ | H | 213–214 | 1620, 1500, 1400, 1340, 1215, 1110 | 425 (M⁺) 394 |
| 77 | (89) | 2-CH₃, 5-CH₃ | 2-OCH₃, 4-OCH₃ | H | 220–221.5 | 1615, 1505, 1410, 1215, 1160, 1040 | 385 (M⁺) 370 |

TABLE 3-continued

| Example | Compound No. | R¹ | R² | R³ | m.p./° C. | I.R./cm⁻¹ | MS |
|---|---|---|---|---|---|---|---|
| 78 | (90) | 2-OCH₃, 5-OCH₃ | 2-OCH₃, 4-OCH₃ | H | 177–177.5 | 3440, 1615, 1515, 1210, 1030 | 417 (M⁺) 386 |
| 79 | (93) | 2-OCH₃, 5-Cl | 2-OCH₃, 4-OCH₃ | H | 203.5–205 | 3450, 1600, 1510, 1420, 1210, 1030 | 392 (M − 1) 390 (M − 1) |
| 80 | (110) | 3-Cl | 4-COOEt | H | 173–174 | 1710, 1590, 1500, 1410, 1270, 770 | 405 (M⁺) 403 (M⁺) 402 |
| 81 | (111) | 3-CF₃ | 4-COOEt | H | 215.5–216.5 | 1710, 1625, 1495, 1400, 1330, 1270 | 437 (M⁺) 386 |
| 82 | (108) | 2-OCH₃, 5-OCH₃ | 4-COOEt | H | 201.5–202.5 | 3300, 1710, 1480, 1400, 1270, 1100 | 397 (M⁺) 382 |
| 83 | (109) | 2-OCH₃, 5-OCH₃ | 4-COOEt | H | 198–199.5 | 3440, 1725, 1600, 1560, 1270, 1090 | 429 (M⁺) 398 |
| 84 | (112) | 2-OCH₃, 5-Cl | 4-COOEt | H | 206–207.5 | 3435, 1725, 1600, 1510, 1420, 1270 | 435 (M⁺) 433 (M⁺) 402 |
| 85 | (119) (120) | 3-Cl | H | 6-CH₃, 7-CH₃ mix | 221–223 | 1590, 1475, 1400, 1250, 770 | 347 (M⁺) 345 (M⁺) 344 |
| 86 | (121) (122) | 3-CF₃ | H | 6-CH₃, 7-CH₃ mix | 221–222.5 | 1600, 1440, 1400, 1330, 1150, 1110 | 379 (M⁺) 378 |
| 87 | (115) (116) | 3-CH₃, 5-CH₃ | H | 6-CH₃, 7-CH₃ mix | 164–168 | 1620, 1500, 1410, 800 | 339 (M⁺) 324 |
| 88 | (117) (118) | 2-OCH₃, 5-OCH₃ | H | 6-CH₃, 7-CH₃ mix | 192–193 | 3430, 1600, 1520, 1450, 1210, 1035 | 371 (M⁺) 340 |
| 89 | (123) (124) | 2-OCH₃, 5-Cl | H | 6-CH₃, 7-CH₃ mix | 146–147.5 | 3430, 1600, 1510, 1420, 1240, 1210 | 377 (M⁺) 375 (M⁺) 344 |
| 90 | (125) | H | H | 6-CH₃, 7-CH₃ | 238–239 | 1605, 1500, 1410, 750 | 325 (M⁺) 324 |
| 91 | (130) | 3-Cl | H | 6-CH₃, 7-CH₃ | 243.5–244.5 | 1605, 1500, 1400, 775, 765 | 361 (M⁺) 359 (M⁺) 358 |
| 92 | (131) | 3-CF₃ | H | 6-CH₃, 7-CH₃ | 255–256 | 1615, 1570, 1445, 1420, 1330, 11170 | 393 (M⁺) 392 |
| 93 | (127) | 2-OCH₃, 5-Cl | H | 6-CH₃, 7-CH₃ | 153.5–156 | 1600, 1575, 1440, 810, 770 | 353 (M⁺) 338 |
| 94 | (128) | 2-OCH₃, 5-OCH₃ | H | 6-CH₃, 7-CH₃ | 232–233 | 3450, 1610, 1520, 1400, 1220, 1010 | 385 (M⁺) 354 |
| 95 | (132) | 2-OCH₃, 5-Cl | H | 6-CH₃, 7-CH₃ | 237–238 | 3450, 1600, 1520, 1425, 1250, 1020 | 391 (M⁺) 389 (M⁺) 358 |
| 96 | (138) | H | H | 6-OCH₃, 7-OCH₃ | 205.5–207 | 1620, 1500, 1410, 1220, 1100, 750 | 357 (M⁺) 356 |
| 97 | (141) | 3-Cl | H | 6-OCH₃, 7-OCH₃ | 199.5–204 | 1620, 1600, 1520, 1410, 1220, 775 | 393 (M⁺) 391 390 |
| 98 | (142) | 3-CF₃ | H | 6-OCH₃, 7-OCH₃ | 223–226 | 1610, 1510, 1400, 1330, 1155, 1115 | 425 (M⁺) 424 |
| 99 | (139) | 2-CH₃, 5-CH₃ | H | 6-OCH₃, 7-OCH₃ | 192–193.5 | 1610, 1510, 1410, 1250, 1210 | 385 (M⁺) 370 |
| 100 | (140) | 2-OCH₃, 5-OCH₃ | H | 6-OCH₃, 7-OCH₃ | 158–158 | 3440, 1610, 1510, 1410, 1215, 1080 | 417 (M⁺) 386 |
| 101 | (143) | 2-OCH₃, 5-Cl | H | 6-OCH₃, 7-OCH₃ | 211.5–213 | 3440, 1610, 1590, 1510, 1410, 1240 | 423 (M⁺) 421 (M⁺) 390 |
| 102 | (144) | 4-C₄H₉ | H | 6-OCH₃, 7-OCH₃ | 187.5–189 | 2920, 1615, 1495, 1405, 1240, 1090 | 413 (M⁺) 412 |

TABLE 3-continued

| Example | Compound No. | $R^1$ | $R^2$ | $R^3$ | m.p./° C. | I.R./cm$^{-1}$ | MS |
|---|---|---|---|---|---|---|---|
| 103 | (145) | 4-OC$_4$H$_9$ | H | 6-OCH$_3$, 7-OCH$_3$ | 183.5–186 | 2940, 1615, 1500, 1405, 1220, 825 | 429 (M$^+$) 372 |
| 104 | (151) | 3-Cl | H | 6-Cl, 7-Cl | 248–250 | 1600, 1480, 1405, 1090, 890, 760 | 403 (M$^+$) 402 (M$^+$) 401 (M$^+$) 400 |
| 105 | (152) | 3-CF$_3$ | H | 6-Cl, 7-Cl | 243–244.5 | 1610, 1515, 1450, 1415, 1335, 1110 | 435 (M$^+$) 434 (M$^+$) 433 (M$^+$) 432 |
| 106 | (149) | 2-CH$_3$, 5-CH$_3$ | H | 6-Cl, 7-Cl | 204–205.5 | 1605, 1560, 1495, 1400, 1380 | 395 (M$^+$) 393 (M$^+$) |
| 107 | (150) | 2-OCH$_3$, 5-OCH$_3$ | H | 6-Cl, 7-Cl | 199.5–201 | 3435, 1610, 1560, 1460, 1210 | 427 (M$^+$) 425 (M$^+$) 394 |
| 108 | (153) | 2-OCH$_3$, 5-Cl | H | 6-Cl, 7-Cl | 201–202 | 3435, 1600, 1550, 1500, 1420, 1250 | 431 (M$^+$) 429 (M$^+$) 400 |
| 109 | (202) | 2-OCH$_3$, 5-Cl | 4-COOH | H | 274–275.5 | 3440, 1690, 1600, 1510, 1420, 1240 | 405 (M$^+$) 374 |

BIOLOGICAL EFFECTS

Compound No. 17, 1-(3-chloroanilino)-4-phenylphthalazine, was assayed for its effect on the human colon carcinoma cell line, HT-29 obtained from ATCC, (Rockville, Md.) to ascertain the degree of growth inhibition. Growth inhibition of this cell line is thought to be indicative of a benefit on precancerous lesions and neoplasms. The cell line and growth assay employed for these experiments is well characterized, and is used by the United States National Cancer Institute in its screening program for new anti-cancer drugs.

Drug stock solutions were made in 100% DMSO then diluted with RPMI media for cell culture testing. All drug solutions were prepared fresh on the day of testing. The cultured cells were obtained at passage #118 and grown in RPMI media supplemented with 5% fetal calf serum, and 2 mM glutamine, 100 U/ml penicillin, 100 U/ml streptomycin, and 0.25 µg/ml amphotericin. The cultures were maintained in a humidified atmosphere of 95% air and 5% CO$_2$ at 37° C. The cultures were passaged at preconfluent densities using a solution of 0.05% trypsin and 0.53 mM EDTA. All experiments involved HT-29 cells between passages 120 and 140. Cells were plated at the following densities to obtain cultures used for the experiments: 500 cells/well for 96 well flat-bottom microtiter plates, 1×10$^6$ cells per 25 cm$^2$ flask, or 4×10$^6$ cells per 75 cm$^2$ flask.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with six wells per drug concentration. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug in Table 4 below.

TABLE 4

Growth Inhibitory Effects for Compound No. 17

| Treatment | SRB Binding (A550) | % Inhibition |
|---|---|---|
| Vehicle | 0.801 ± 0.137 | 0 |
| No. 17 (1 µM) | 0.851 ± 0.059 | 0 |
| No. 17 (10 µM) | 0.007 ± 0.003 | 100 |
| No. 17 (100 µM) | 0.009 ± 0.010 | 100 |

Apoptosis and necrosis were measured using an assay which allowed for the simultaneous measurement of both types of cell death based on morphological characteristics of apoptotic cells (i.e., condensed chromatin) and membrane permeability. Drug preparation and cell culture conditions were the same as above. Confluent cultures were assayed for apoptosis and necrosis by fluorescent microscopy following labeling with acridine orange and ethidium bromide. Floating and attached cells were collected by trypsinization and washed three times in PBS. One ml aliquots of 1×10$^6$ cells were centrifuged (300 g). The pellet was resuspended in 25 µl media and 1 µl of a dye mixture containing 100 µg/ml acridine orange and 100 µg/ml ethidium bromide prepared in PBS and mixed gently. Ten µl of mixture was placed on a microscope slide and with a 22 mm$^2$ coverslip and examined under 40 x dry objectives using epilumination and filter combination.

An observer blinded to the identity of the treatments scored at least 100 cells per sample. Apoptotic cells were identified by nuclear condensation of chromatin stained by the acridine orange or ethidium bromide. Necrotic cells were identified by uniform labeling of the cell with ethidium bromide. These results are provided in Table 5 below.

TABLE 5

Apoptosis and Necrosis Effects for Compound No. 17

| Treatment Cells | % Apoptotic Cells | % Necrotic |
|---|---|---|
| None | 7 | 5 |
| Vehicle | 9 | 2 |
| No. 17 (40 μM) | 83 | 6 |

Data was also obtained, under the same procedure above, for the percent of apoptotic cells induced by treatment with varying concentrations of compound No. 17. These results are provided in Table 6 below.

TABLE 6

Apoptosis vs. Varying Concentrations of Compound No. 17

| Drug Concentration (μM) | % Apoptotic Cells |
|---|---|
| 0 | 4 |
| 1 | 12 |
| 5 | 13 |
| 10 | 7 |
| 25 | 8 |
| 50 | 78 |

Compound No. 17 was also tested for its ability to inhibit the incidence of mammary lesions in an organ culture system. This mouse mammary gland organ culture technique has been successfully used by other investigators to study the effects of known cancer-chemopreventative agents such as retinoids and selenium.

Female BALB/c mice, 28 days old, were treated for nine days with a combination of 1 Ag of estradiol and 1 mg of progesterone daily, in order to prime the glands to be responsive to hormones in vitro. The animals were sacrificed and thoracic mammary glands were excised aseptically and incubated for ten days in growth media supplemented with growth-promoting hormones: insulin, prolactin, and hydrocortisone, at 5 μg/ml each and aldosterone at 1 μg/ml. A twenty-four hour treatment of 7,12-dimethylbenz(a)anthracene (DMBA, 2 μg/ml) was carried out between days three and four to induce the formation of mammary lesions. Fully developed glands were deprived of prolactin, hydrocortisone, and aldosterone for 14 days, resulting in the regression of the glands but not the mammary lesions.

In order to evaluate the effects of Compound No. 17, it was dissolved in DMSO and added to the culture media supplemented for the duration of the culture period. At the end of the culture period, the glands were fixed in 10%. formalin, stained with alum carmine, and mounted on glass slides. The incidence of forming mammary lesions is the ratio of the glands with mammary lesions and glands without lesions. The incidence of mammary lesions in compound 17 treated glands was compared with that of the untreated glands.

The extent of the area occupied by the mammary lesions was quantitated by projecting an image of the gland onto a digitation pad. The area covered by the gland was traced on the pad and considered as 100% of the area. The space covered by each of the unregressed structures was also outlined on the digitization pad and quantitated by the computer.

TABLE 7

Effect of Compound No. 17 on DMBA-Induced Mammary Lesions in Organ Culture

| Drug Concentration (μM) | No. Glands Per Group | Glands with Lesions | Percent Incidence | Percent Inhibition |
|---|---|---|---|---|
| Vehicle | 15 | 11 | 73.33 | 0 |
| No. 17 (10 μm) | 13 | 7 | 53.85 | 27 |
| No. 17 (100 μm) | 15 | 4 | 26.67 | 64 |

Each of the compounds according to the present invention was reported to be very low in toxicity, namely not less than 5000 mg/Kg in terms of $LD_{50}$ as measured by oral administration for mice. Compounds of this invention, therefore, are excellent candidates for long term use as therapeutic agents for precancerous lesions.

The compounds of Examples 1–253 can be formulated with pharmaceutically acceptable carriers into unit dosage forms in a conventional manner so that the patient in need of therapy for precancerous lesions can periodically (e.g. once or more per day) take a compounds according to the method of this invention.

The exact initial dose of the 4-phenylphthalazine derivatives used in the method of this invention can be determined with reasonable experimentation. However, it is believed that the initial dose may be between about 0.03 mg/day and about 14.0 mg/day in the average adult.

It will be understood that various changes and modifications can be made in the details of procedure, formulation and use without departing from the spirit of the invention, especially as defined in the following claims.

We claim:

1. A method of treating a patient in need of treatment having precancerous lesions sensitive to a compound of formula I, comprising administering to the patient a pharmacologically effective amount of a compound of formula I:

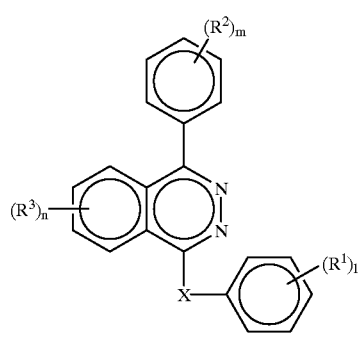

(I)

wherein X stands for NH or O;

$R^1$ is selected from an alkyl group having 1 to 5 carbon atoms, an alkoxy group having 1 to 5 carbon atoms, a halogen atom, an alkoxycarbonyl group having 2 to 6 total carbon atoms, a carboxyl group, a cyano group, an alkylcarbonyl group having 2 to 4 total carbon atoms, a hydroxyl group and a trifluoromethyl group;

$R^2$ and $R^3$, which may be identical or different (may also be the same as or different from $R^1$), each is selected from an alkyl group having 1 to 5 carbon atoms, an alkoxy group having 1 to 5 carbon atoms, a halogen atom, an alkoxycarbonyl group having 2 to 6 total carbon atoms, a carboxyl group, an alkylcarbony group having 2 to 4 total carbon atoms, a hydroxyl group and a trifluoromethyl group; and each of l, m and n is an integer of zero to 3 (provided that l=1 to 3 and m=n=zero when X is O, and the case where l=m=n=zero is excluded when X is NH), each plural number of $R^1$, $R^2$ and $R^3$ being identical or different when the integers l, m and n are two or more.

2. The method of claim 1, wherein X is NH.

3. The method of claim 2, wherein l=1 to 3 and m=n=zero.

4. The method of claim 3, wherein $R^1$ is selected from an alkyl group, an alkoxy group, a halogen atom and a trifluoromethyl group.

5. The method of claim 3, wherein $R^1$ is selected from an alkoxy group and a halogen atom.

6. The method of claim 5, wherein $R^1$ is a halogen.

7. The method of claim 6, wherein said compound is 1-(3-chloroanilino)-4-phenylpthalazine.

8. The method of claim 2, wherein l=1 to 2, m=1 to 2 and n=zero.

9. The method of claim 2, wherein l=1 to 2, m=zero and n=1 to 2.

10. The method of claim 2, wherein l=m=zero and n=1.

11. The method of claim 1, wherein X is O.

12. The method of claim 11, wherein l=1 to 3 and m=n=zero.

13. The method of claim 12, wherein l=1 to 2.

14. The method of claim 1, wherein $R^1$ and $R^2$ are independently selected from an alkyl group, an alkoxy group, a trifluoromethyl group and a halogen atom.

15. The method of claim 14, wherein $R^3$ is an alkyl group.

16. The method of claim 15, wherein $R^1$ is selected from an alkoxy group and a halogen atom.

17. The method of claim 16, wherein $R^1$ is a halogen atom.

18. The method of claim 17, wherein m=n=zero and l=1 to 3.

19. The method of claim 18, wherein X is NH.

20. A method for inhibiting the growth of neoplastic cells sensitive to compound of formula I, comprising exposing said cells to an effective amount of a compound of formula:

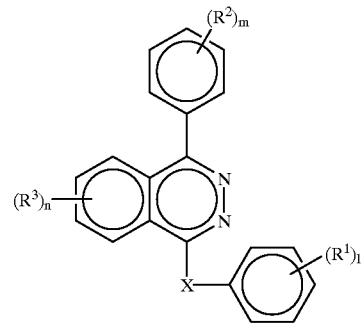

(I)

wherein X stands for NH or O;

$R^1$ is selected from an-alkyl group having 1 to 5 carbon atoms, an alkoxy group having 1 to 5 carbon atoms, a halogen atom, an alkoxycarbonyl group having 2 to 6 total carbon atoms, a carboxyl group, a cyano group, an alkylcarbonyl group having 2 to 4 total carbon atoms, a hydroxyl group and a trifluoromethyl group;

$R^2$ and $R^3$, which may be identical or different (may also be the same as or different from $R^1$), each is selected from an alkyl group having 1 to 5 carbon atoms, an alkoxy group having 1 to 5 carbon atoms, a halogen atom, an alkoxycarbonyl group having 2 to 6 total carbon atoms, a carboxyl group, an alkylcarbony group having 2 to 4 total carbon atoms, a hydroxyl group and a trifluoromethyl group; and each of l, m and n is an integer of zero to 3 (provided that l=1 to 3 and m=n=zero when X is O, and the case where l=m=n=zero is excluded when X is NH), each plural number of $R^1$, $R^2$ and $R^3$ being identical or different when the integers l, m and n are two or more.

21. The method of claim 20, wherein l=1 to 2, m=n=zero and X=NH.

22. The method of claim 21, wherein $R^1$ is selected from an alkyl group, an alkoxy group, a halogen atom or a trifluoromethyl group.

23. The method of claim 22, wherein $R^1$ is selected from an alkoxygroup and a halogen atom.

* * * * *